(12) United States Patent
Möllstam et al.

(10) Patent No.: US 8,801,654 B2
(45) Date of Patent: *Aug. 12, 2014

(54) METHOD AND DEVICE FOR IRRIGATION OF BODY CAVITIES

(75) Inventors: Anders Möllstam, Saltsjö Boo (SE); Sven Milton, Vikingstad (SE); Tomas Movin, Huddinge (SE)

(73) Assignee: Medical Vision AB, Nacka (SE)

( * ) Notice: Subject to any disclaimer, the term of this patent is extended or adjusted under 35 U.S.C. 154(b) by 1535 days.

This patent is subject to a terminal disclaimer.

(21) Appl. No.: 11/729,357

(22) Filed: Mar. 28, 2007

(65) Prior Publication Data

US 2007/0249993 A1    Oct. 25, 2007

(30) Foreign Application Priority Data

Mar. 30, 2006  (SE) ...................................... 0600718

(51) Int. Cl.
| | | |
|---|---|---|
| *A61M 1/00* | (2006.01) | |
| *A61B 1/015* | (2006.01) | |
| *A61B 1/12* | (2006.01) | |
| *A61M 3/02* | (2006.01) | |

(52) U.S. Cl.
CPC ............... *A61B 1/125* (2013.01); *A61B 1/015* (2013.01); *A61M 3/0258* (2013.01); *A61M 2205/331* (2013.01); *A61B 1/126* (2013.01)
USPC ................................ 604/31; 604/67; 604/118

(58) Field of Classification Search
CPC ............ A61M 1/0058; A61M 5/1723; A61M 2205/33; A61M 2205/3306; A61M 2205/3313; A61M 2205/3334; A61M 2205/3344; A61M 2205/3351; A61M 2205/3355

USPC ................. 604/27, 30, 31, 65, 67, 118, 119; 250/573

See application file for complete search history.

(56) References Cited

U.S. PATENT DOCUMENTS

| | | |
|---|---|---|
| 3,979,290 A | 9/1976 | Loffler |
| 4,168,700 A | 9/1979 | Opelt et al. |

(Continued)

FOREIGN PATENT DOCUMENTS

| | | |
|---|---|---|
| EP | 0 529 902 A2 | 3/1993 |
| GB | 2 260 622 A | 4/1993 |
| WO | PCT/SE84/00258 | 1/1986 |

*Primary Examiner* — Kami A Bosworth
(74) *Attorney, Agent, or Firm* — Renner, Otto, Boisselle & Sklar, LLP (57) ABSTRACT

A pressure and a vision regulation method and device for irrigation of a body cavity (1), in which an inflow liquid pump (2) pressurizes the irrigation liquid in a feed line (13) and an outflow device (3) or an external suction source (20) drains the irrigation liquid from the body cavity (1) through a tubing (16) into a waste container (17). A control unit (4) controls either the inflow liquid pump (2) only or both the inflow liquid pump (2) and the outflow device (3) depending on an inflow irrigation liquid pressure from a pressure sensor (5). The method and the device are combined with a method for detecting blood cells, red blood cells, haemoglobin and/or debris in liquid coming from a surgical site to provide an automatic control and rinsing system with clear vision in the viewing area of the operational site.

7 Claims, 7 Drawing Sheets

(56) References Cited

U.S. PATENT DOCUMENTS

| | | |
|---|---|---|
| 4,795,424 A | 1/1989 | Burner |
| 4,998,914 A | 3/1991 | Wiest et al. |
| 5,520,638 A | 5/1996 | O'Quinn et al. |
| 5,586,973 A | 12/1996 | Lemaire et al. |
| 6,175,420 B1 * | 1/2001 | Barry et al. .................. 356/436 |
| 6,396,583 B1 * | 5/2002 | Clare ............................ 356/436 |
| 6,517,512 B1 * | 2/2003 | Bock et al. ...................... 604/67 |
| 2003/0236488 A1 | 12/2003 | Novak |
| 2004/0133149 A1 * | 7/2004 | Haischmann et al. .......... 604/31 |
| 2006/0175561 A1 | 8/2006 | Estevadeordal et al. |

\* cited by examiner

METHOD AND DEVICE FOR IRRIGATION OF BODY CAVITIES

CROSS-REFERENCE TO RELATED APPLICATIONS

This application claims priority from Swedish application no. 0600718-1 filed Mar. 30, 2006.

TECHNICAL FIELD OF THE INVENTION

This invention relates to the medical field of endoscopic surgery, and in particular the management of liquid that is irrigated into the surgical site during endoscopic procedures.

BACKGROUND OF THE INVENTION

During endoscopic surgical procedures, a surgical site such as a knee joint, shoulder joint or other cavity in the body of a human or animal is viewed with an endoscope. Further in this patent application, the surgical site for an endoscopic procedure is referred to as the body cavity. The body cavity is irrigated with a clear liquid by means of a pump. This pump is further in this patent application referred to as an inflow liquid pump. The clear liquid is as a rule saline, and the pump is usually a peristaltic roller type pump.

Existing liquid management systems are either operated by a fixed flushing volume programmed by the operator of the system when starting the procedure (normally an ml/min value), or by a fixed pressure target for the system. This target pressure is selected by the operator of the system when starting the process. Existing pressure controlled systems have different ways of measuring the pressure, but the overall technique is to directly or indirectly measure the pressure on the irrigation side of the system. The limitation with the volumetric system is that an excessive liquid volume is needed to achieve a rinsing effect. The limitations with the fixed pressure target systems are firstly that it is impossible to flexibly change the pressure depending on the needs during the operation. Thereby an unnecessary high pressure is used in many cases resulting in tissue swelling and subsequently a risk of tissue damage. Secondly the fixed pressure controlled systems seldom operate at the fixed pressure target as the systems are based on the measurement of an indirect pressure in the operation site. When the operation site is drained of liquid it takes some time for such a system to react to a lower pressure due to volume/pressure hysteresis of the tissue, and the reaction time can sometimes be very long resulting in an unnecessarily long time of bad visibility during the endoscopic procedure.

With both the volumetric- and the fixed pressure target systems the body cavity expands as a result of the pressure from the irrigation, and the inside of the body cavity can be viewed with an endoscope. The pressure value of the saline solution is an important matter. The higher pressure, the better viewing of the area is accomplished. Also, the pressure holds back blood from vessels that are damaged as a normal effect of the surgical process. Emerging blood obstructs visibility, and it is of course in general desirable to stop bleeding during surgery. The pressure causes tension in the tissue. However, too high a pressure may cause tissue damage, which must be avoided as much as possible. Thus, a precise control of pressure in the body cavity is of vital importance. It is well known how to measure pressure in a liquid, but a direct measuring of pressure in the body cavity is not possible without introducing pressure measuring sensors together with the surgical instruments into the body cavity. However, this method is bulky, expensive and difficult to operate. Alternatively, body cavity pressure can be measured by making an extra perforation of the body for the introduction of a pressure-measuring sensor into the body cavity. The latter makes the surgical procedure more complex, and also causes inconvenience and risk to the patient.

Another problem with endoscopic procedures is that aforementioned blood in the body cavity reduces visibility. Also, the surgical procedures as a rule involve the removal of, or work on tissue, for instance the meniscus of the knee. This results in debris, namely particles of various sizes of tissue floating around in the liquid in the body cavity. This also reduces visibility for the surgeon. These difficulties are routinely managed by rinsing. To rinse out blood or debris, the liquid in the body cavity is replaced by introducing or increasing liquid flow through the body cavity. The pressure may optionally be temporarily elevated. This may stop bleeding as the pressure in the body cavity exceeds that of the blood pressure in the ruptured blood vessels in the body cavity. If the introduction of liquid is made with an inflow liquid pump, the operation is started by pressing a button, or by a foot-operated switch. However, if the outflow of liquid simultaneously is affected, introducing or increasing liquid outflow causes the pressure in the body cavity to drop. If the situation is severe, the flow necessary to rinse the body cavity may have to be very high, and this inevitably causes a significant drop in pressure, and could indirectly be dangerous to the patient as the surgeon is distracted. Furthermore, in some cases the pressure does in fact not drop as a rinse process is initiated. Instead, the body cavity is drained of liquid, but the pressure drops only insignificantly and a pressure regulation function does not foresee that the body cavity is drained. This is due to a high compliance of the body cavity, and in this example this may be the case if the body cavity is a shoulder or a urine bladder. The end result in this case is that the viewing area becomes too small for viewing with the endoscope, but the pressure nearly persists. These repeating obstructions of visibility can be disturbing for the surgeon, and also calls for some action from the user to change pressure, flow or the user may have to wait for quite some time for the situation to stabilize.

DE 3338758, GB 2260622 A, US 2003/0236488 A1, US 2004/0133149 A1, WO 86/00534 and EP 529902 all disclose a method to regulate pressure in an endoscopy system by means of a pressure transducer at the body cavity side of an inflow pump, and a regulating function of the inflow pump. All systems have in common the regulation of pressure of the inflow pump, as the generated pressure is measured by or near it.

In U.S. Pat. No. 5,520,638 a pressure measurement principle is disclosed, using an air filled bladder in the pressurized liquid. The pressurized air transfers the air pressure to a pressure transducer in the inflow pump system. The air filled bladder must be connected to a panel connector via an air line and connector. The major disadvantage of these solutions is that there is a risk of leakage in the air connection to the pump. Such leakage increases the pressure to levels that may endanger the patient, as pressure control is lost. Another disadvantage of these solutions is that the pressure by the pump is much higher than in the body cavity as a result of the resistance of flow in the irrigating system. The pressure generated by the inflow pump is controlled by measuring the pressure by the inflow pump itself. The control mechanism in the above mentioned references is a regulating function, where the generated pressure is measured via air filled tubing to a pressure transducer, or by measuring the pressure indirectly by detecting the small expansion of the tubing. The rotational speed of the inflow pump is set to maintain a preferred pressure.

In U.S. Pat. No. 5,556,378, a device is disclosed that measures the pressure difference between a pump irrigating a body cavity, and a suction pump removing liquid from the site. With this system it is complicated, however, to maintain a steady pressure in the body cavity, and two pressure measuring sensors and a complex system are necessary for a desired result. Also, control of flow is basically lost to achieve a desired pressure. This is highly undesirable, as flow should be under control during rinsing procedures, and minimized in between actions of rinsing.

In U.S. Pat. No. 4,998,914 a method to compensate for the conductance of the fluid line is disclosed. This is a way to measure pressure in the body cavity by an indirect method, but the method does not take flow changes into account. Thus, the pressure drop that occurs during a rinsing procedure is not compensated for.

OBJECT OF THE INVENTION

The object of the present invention is to provide for a device and a method for irrigation of body cavities under the independent control of pressure and flow through the cavities.

Another object of the invention is to provide for a device and a method for irrigation of body cavities depending on the detection of blood cells, red blood cells, haemoglobin and/or debris from the surgical site.

The invention enables achievement of control over the pressure in, and flow through, the surgical site, the detection of blood cells, red blood cells, haemoglobin and/or debris from the surgical site, the detection of blood lost from the surgical site, and control of the flow and pressure through the surgical site by use of signals from detectors detecting blood cells, red blood cells, haemoglobin and/or debris from the surgical site.

It also provides for the detection of the pressure in the body cavity without the introduction of instrumentation for pressure measurement.

The object of the invention is also to provide for a process to actively remove the liquid from the body cavity by means of a second pump or other suction source, also usually a peristaltic roller type pump. This process is referred to herein as an outflow device or outflow liquid pump.

SUMMARY OF THE INVENTION

The objects of the invention are achieved by means of the present invention as defined in the accompanying independent claims. Suitable further embodiments will be apparent from the accompanying dependent claims.

The present invention presents a new indirect method to measure pressure in the body cavity such as that of a knee or shoulder during endoscopy procedures. When the body cavity is irrigated, a peristaltic inflow pump generates a pressure; $P_{pump}$. The pressurized liquid is fed via tubing to a viewing instrument such as an endoscope, or another instrument such as a large needle or similar means for irrigation of liquid into the body cavity. Due to resistance in the liquid pathway, there is a loss of pressure. This pressure loss subsists all the way from the inflow pump to the body cavity, and varies by various components forming the liquid path. The pressure loss is higher the smaller the lumen of the liquid pathway is, and the higher the flow is. It is to be noted that the resistance value is not linear with respect to flow. Flow turbulence in the irrigation system causes unlinearities. This is why the resistance of the tubing and instrumentation has to be established by the following method: The resistance values for relevant flow values are established and entered into an electronic memory in the pump system of the invention. This establishment is done in two ways: Initially, at production of the system, the pressures are measured at all relevant flows and input pressures, $P_{pump}$ and pressures in the body cavity, $P_{cavity}$, in a laboratory environment. Thus, a pressure measured at the input of the system corresponds to an achieved pressure in the body cavity. The pressure in the body cavity is measured to establish $P_{cavity}$. This establishment can be made by use of various models for the body cavity such as a knee model, urine bladder model, uterus model etc. The hydrostatic pressure $P_{hyd}$, caused by the difference in height between the pressure transducer and the body cavity should be taken into account. Preferably this should be zero; in other words the calibration is made as the pressure transducer is at the same level as the body cavity. The pressures are noted for each relevant flow step, such as for every 5 ml/min step, and stored permanently in the pump system memory. Several sets of resistance values are established, one for each relevant cassette/tubing/instrumentation setup. If $P_{hyd}$ is 0, the derived resistance, R can be expressed as:

$$R = \frac{P_{pump} - P_{cavity}}{Flow}$$

Secondly, the resistance in the system is reconfirmed during routine use of the system. This reconfirmation is made by a temporary halt of flow by stopping both the inflow and outflow pumps instantaneously. The outflow pump can alternatively be replaced with a valve, which stops the flow in the same manner. This alternative can be used when the liquid management system only operates an irrigation pump. The valve function may comprise means to pinch tubing. At that instant, the pressure is high at the inflow pump, where the pressure is also measured, and lower in the body cavity. The liquid is trapped between the following components: the roller of the inflow peristaltic pump; the cavity of the pressure transducer; the tubing from the pressure transducer to the endoscope connector with shutoff valve; endoscope connector with shutoff valve; the endoscope; the body cavity; the liquid output from the body cavity such as a cannula, shaver or other instrument; the tubing from the output instrument to the rollers of the outflow peristaltic pump, or a valve function; and finally the rollers of the outflow peristaltic pump or a valve function. During the next phase, being approximately 2 seconds, the pressure difference between the inflow pump and the body cavity causes a diminishing flow to the body cavity. If the time the pumps are stopped is long enough, the pressure difference will diminish by a basic rule of communicating vessels. The time constant of this diminishing flow is a representation of resistance. It is to be noted that it is not necessary to hold the pumps stopped for the time it takes for the flow to become zero. An extrapolation of the pressure signal is fulfilling for the purpose of determining an end pressure. This minimizes the time the body cavity is not irrigated. The reconfirmation can be initialized manually by pressing a button, or automatically by regular intervals controlled by the software, or automatically triggered by software if pressure fluctuations occur that indicate that the surgical situation might have influenced resistance.

As mentioned above, the resistance varies with flow, but it does not vary significantly with pressure. The components from the inflow pump to the body cavity basically do not expand as a result of increased pressure. With the described technique of reconfirming resistance, there is little or no flow at the end of the measuring phase, but the inflow tubing and instrumentation are pressurized. If there is a variation in the measured resistance in the inflow system at the same pressure by this method, this is emerging from expansion of the body cavity. In other words, there is a volumetric change. This expansion is pressure dependent and referred to as the compliance. This compliance, C can be expressed as:

$$C = \frac{V_{1cavity} - V_{2cavity}}{P_{1cavity} - P_{2cavity}}$$

The $V_{1cavity}$ is the first volume in the body cavity, and $V_{2cavity}$ is a second volume in the body cavity. $P_{1cavity}$ is a first pressure in the body cavity and $P_{2cavity}$ is a second pressure in the body cavity.

Compliance values can be calculated by the pump system, which measures the pressure as mentioned above, and the flow is proportional to the rotational speed of the roller pump heads. Calculated compliance values are also stored in a memory, and can be used in several ways. One first consideration is the effect the compliance has on the process of reconfirmation of resistance values. The reconfirmation of resistance values is adjusted for as a result of the compliance as the aforementioned time constant is affected by compliance. Another use of the compliance value is to indicate these to the operator. This has the benefit of warning the operator of the risk that excessive liquid may be introduced. The indication can be that of a figure in a display, a "bar indicator" in a display, or a buzzer that emits sound at a predetermined level of compliance. The compliance value can also affect the operation of the pump system by limiting the pressure it produces, to avoid tissue damage.

The above-mentioned flow/pressure relationship is discussed with a constant flow in mind. If one should take not only a constant static flow into account but also the change in flow, the flow restriction in the tubing and instrumentation is described as impedance. Further, and of importance, is the reactive component of the impedance. The reactive component has a restrictive effect on acceleration of the liquid in the tubing and instrumentation. The consequence is that an initiated change of pressure results in a change of flow after some time. At a nominal pressure and nominal flow for an endoscopy system as described, this flow change is approximately 2 seconds. For utmost control of pressure in the body cavity, this reactance must be taken into account. The decision to increase flow is as a rule fairly urgent. Thus, the pressure that accelerates the liquid has to initially be even higher than the designated pressure by the inflow pump to accelerate the liquid. This can be defined as an overpressure. As the flow is to be increased, the reactive component is compensated for by the overpressure. The reactive component has to be established for various instrument setups as well as the resistance mentioned earlier in this patent application. Also, the flow away from the body cavity can optionally be delayed by introducing a delay of the start of the outflow pump to further enhance a rapid increase in pressure. Alternatively, the outflow pump may increase rotational speed with more or less acceleration, as it takes some time to introduce the elevated pressure in the body cavity. Further, if the rinsing is too intense, the inflow may not be able to provide the necessary flow due to the reactance and resistance in the inflow line. It may be necessary to make a decision if the pressure or rinsing has the highest priority, and this can be made by software or by a manual selection by the user. The software decision can be made on a basis of the compliance calculation mentioned above. The manual selection can be a front panel switch with selection of procedure type "knee", "urine bladder" etc.

In yet another situation, the compliance of the body cavity may be very high. In the case of rinsing an irrigated pressurized body cavity, there may be an elevated outflow but the system would not replace the liquid by maintaining the pressure as described above. Pressure would nearly persist, but the liquid volume in the body cavity would drop. Technically speaking, this is a description of tissue hysteresis, originating from the fact that more force is needed from the pressurized liquid to expand tissue surrounding the body cavity than is needed to maintain the body cavity volume. In this particular situation, the viewing field will eventually diminish as the body cavity "caves in". The reason for this is that residual pressure inhibits a relevant inflow to replace the removed liquid. The inflow pump pressure regulation detects a relatively high pressure, as the body cavity is collapsing and the volume drops. When this particular situation is the case, the system may decide to elevate the speed of the inflow pump to that of the outflow pump to compensate for the drawn liquid. The system must however constantly monitor the pressure, as this may not be elevated too high. The above mentioned solution to maintain the viewing area by replacing drawn liquid with the inflow pump with only careful influence of pressure in the body cavity is most beneficial.

In another aspect of the invention, the degree of blood emerging from the body cavity is detected by use of an optical detector. The detector encompassing the fluid path that leaves the body cavity and comprises at least one light emitting diode (LED). At least one photo detector is measuring the light intensity from the LED's that are irradiating the fluid path with light, and this/these incorporate a light sensitive component, such as a light sensitive transistor or light sensitive diode. As known in the art of detecting haemoglobin or red blood cells, the two sensors can measure a baseline by measuring and storing the light surrounding the detector first as the light emitting diode is off. At a rapid interval, the LED is turned on and off at, for instance, a 50% duty cycle. The light detected when the LED is off represents the surrounding light from lamps, the sun etc. The light detected when the LED is on additionally represents the light that has passed through the liquid from the body cavity. The difference between the light measured when the LED is on and when it is off is the signal output from the sensor. This may be derived by use of a microcontroller process to store the aforementioned two signals, and subtracting them. Another solution is to store the two detected signal levels by use of analog circuitry, such as electronic switches and capacitors, or similar sample and hold circuitry as known in this art.

The detector can be haemoglobin sensitive by use of a suitable light wavelength that is haemoglobin sensitive for the first sensor. In a second sensor, a different wavelength is used, and this different wavelength detects the baseline optical opacity of the liquid leaving the body cavity. The comparison of the two sensors results in a signal that is most sensitive to haemoglobin. This comparison is made by subtraction of the two signals from each detector. This subtraction can be derived by use of a microcontroller process to store the aforementioned two signals, and subtracting them. Another solution is to store the two detected signal levels by use of analog circuitry, such as electronic switches and capacitors or similar sample and hold circuitry, and subtracting the two resulting voltages by use of a differential amplifier.

The optical detector is fitted on the housing for the pump system, but may optionally be fitted near or even directly by or within the surgical instrumentation that is forming the liquid path emerging from the patient, such as a shaver or cannula. The advantage of having the detector mounted on the panel of the pump system is that external wiring is not needed, but detachably fitting the optical detector near or even directly by the surgical instrumentation can be accomplished by use of wireless data transfer and a battery operated detector. If the detector is fitted on or within the housing of a shaver, the wiring for the optical detector may be enclosed in the cable for the shaver. The invention can trigger a signal to the operator, if blood is detected.

In another aspect of the invention, the signal values from the blood cells, red blood cells or haemoglobin detection are periodically accumulated in the memory of the processor or in another electronic memory. These accumulated values form a sum of signal values throughout the surgical process. This sum can be multiplied by a calibration factor, and thus be indicative of the amount of blood that has emerged from the patient as a result of the surgical process. This amount of lost blood can be displayed on the instrument display. Furthermore this blood loss can trigger an alarm to the operator, when the detected blood loss has reached a predetermined level.

In another aspect of the invention, the signals from the aforementioned optical sensors are used to detect the absorbance of light of the liquid emerging from the body cavity, as debris originates as a result of the surgical process. This detection is formed by initially detecting and storing the signal from one or both sensors as there is liquid in the optical path. This liquid is clear and thus has a minimum absorbance. This first signal level may be established during a calibration process in conjunction with manufacture, but also in the process of starting up a process of normal use. Having established this first signal, it is constantly compared to the signals from both aforementioned optical sensors during further use of the pump system during a surgical procedure. Furthermore, this debris detection takes advantage of the signal processing of the sensor or sensors as mentioned above in a previous embodiment. The detection of debris is established either from one of the two sensors, or both. The signal from the detector is both that of a rapidly fluctuating signal, as debris is passing by the detector, and an offset with smaller fluctuations representing fine homogenous "milky" substance that appears as a fog when viewed with the endoscope. A signal process detects the intensity of the fluctuations or the depth of absorbance, or both, as indicators of debris in the liquid.

Optionally, a second sensor may be engaged in the inflow system: Anywhere in the liquid path from the source of liquid to the endoscope, the liquid is clear of blood or debris, and may be used as a reference value for detecting blood or debris in the liquid path from the patient.

The disposable material by the optical detector in the outflow path may be smudged with body fats as a result of the surgical process. The signal processing can compensate for this slow build up of offset of signal from the optical detector.

Rinsing of the body cavity may be initiated manually by the press of a button or a foot operated switch, and results in an increased liquid flow. However the detection of blood or debris may automatically initiate a rinsing process. This detection may in general increase flow through the body cavity and this will beneficially keep the liquid clear. Such increase may be gradual or in steps to achieve the target of a clear viewing filed for the surgeon. Whether decided by a user or automatically by the system, the rinsing of the body cavity can be terminated manually or automatically. Optionally the pressure may be elevated to depress bleeding. This elevation of pressure is preferred as blood is detected, but not debris. Increasing pressure over the patients' perfusion blood pressure reduces the bleeding. The result is that a clear viewing field is maintained automatically and the operator can focus on the endoscopic procedure instead of manually optimizing the liquid management system to give visibility. The operation time will thereby be reduced in most procedures resulting in fewer complications for the patient.

The present invention pressure registration method and the device for irrigation of a body cavity is combined with a method for detecting blood cells, red blood cells, haemoglobin and/or debris in liquid coming from a surgical site so an automatically control and rinsing system is achieved keeping a clear view in the viewing area of the operational site.

BRIEF DESCRIPTION OF THE DRAWINGS

The invention will now be described in more detail by means of an embodiment example with reference to the accompanying drawings.

DESCRIPTION OF THE INVENTION

When a body cavity is irrigated, a peristaltic inflow pump generates a pressure. Due to resistance in the liquid pathway, there is a loss of pressure along it. This pressure loss subsists all the way from the inflow pump to the body cavity, and varies by various components forming the liquid path. The higher the flow, the higher the resistance. This resistance is not linear with respect to flow. At the design of an irrigation system, the resistance values for relevant flow values are to be established in a laboratory environment. Thus, a pressure measured at the input of the system corresponds to an achieved pressure in the body cavity. Then the measured "actual" values for the pressures in the body cavity can be calculated from the flow and the established resistance.

The method to establish the pressure in the body cavity without measuring pressure in it is further enhanced in the following way: When there is a need for a change in flow or pressure, the acceleration of the liquid is firmly enforced by over pressure from the inflow pump. In that fashion, the inductive (reactive) components of the liquid path are accounted and compensated for. The end result is a control over pressure in the body cavity that overcomes the resistance and reactance in all aspects in the liquid flow path.

The pump system controls the flow by the rotational speed of two roller pumps. Both the irrigation liquid and the liquid that is extracted from the body cavity are individually controlled. The invented irrigation system keeps track of liquid administration by memorizing the number of turns the inflow and outflow roller pumps are completing. A difference in inflow and outflow of liquid indicates how much liquid is introduced into the body cavity and its surroundings. Should the pump system deliver a higher inflow than outflow, pressure in the body cavity is increasing. By analyzing the pressure and flow, the compliance can be calculated. Also, the amount of liquid that leaves the body cavity can be calculated. This is done in the following way: With a stabilized pressure, nominally, there is no liquid loss. If liquid leaves the body cavity, the inflow pump needs to make more turns than the outflow pump to maintain a constant pressure. A slow or minor increase in such liquid loss indicates that the liquid is leaving the surgical site, but stays within the immediate surroundings of the surgical site. The difference in number of rotational turns the pump heads complete represents such lost liquid volume. The pump system can record and/or alarm when predetermined values of liquid are leaving the body cavity into tissue surrounding the body cavity or are leaking out from the surgical site through any of the ports used for instruments. It is highly beneficial to the user to get an indication of leakage. The leakage out from the operational site is visible for the operator but leakage into tissue is normally difficult to detect. If above mentioned liquid loss is increasing very rapidly, it is indicative of a mechanical or technical circumstance, such as a leakage in a connector, and should not be inclusive in the calculated amount of liquid introduced into the body. At such stage of liquid loss, the pump may stop and/or give an alarm.

During an endoscopy procedure, it will periodically be necessary to rinse the body cavity from blood and debris. This is basically done by initiating or increasing flow through the body cavity.

To furthermore secure pressure and flow control, the pump system outflow pump follows that of the inflow pump during a rinse procedure. Shortly after flow is increased, as described above, the outflow pump follows the same rotational speed as the inflow pump, relevant for the new desired elevated flow. The system must however constantly monitor the pressure, as described above, as this may not be elevated too high. In many cases of endoscopic surgery this solution to maintain the viewing area by immediate replacement of drawn liquid with the inflow pump irrespective of pressure in the body cavity is most beneficial.

Figure 1:
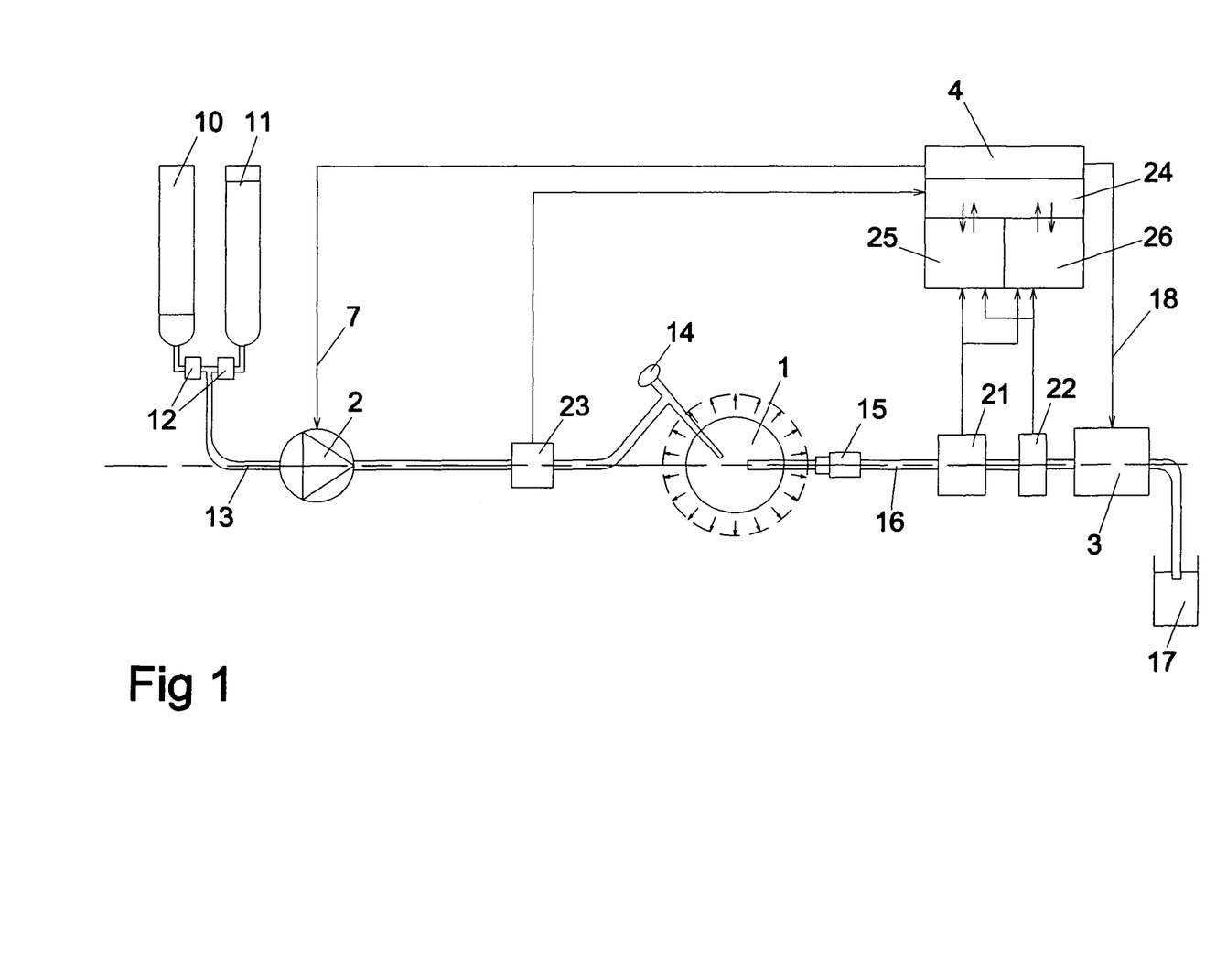
FIG. 1 shows a first feature of the invention.

FIG. 1 shows a first feature of the invention as a pump system for use in irrigating a body cavity 1 which pump system comprises an inflow liquid pump 2, an outflow device 3 and a first control unit 4 containing electronics with a microcontroller for the drive of the pumps, memory circuits including a calculating function unit, front panel, power supply etc. Also, a pressure sensor can be electrically connected to the first control unit by a signal line through which an electric signal corresponding to the actual liquid pressure is delivered to the control unit, (not indicated in FIG. 1). The first control unit 4 is also electrically connected to the inflow liquid pump 2 by an input pump signal line 7. The pump system withdraws saline from a first container 10 by means of the pump of the inflow liquid pump 2, preferably being a peristaltic roller pump. The first container 10 may cooperate with a second container 11 by means of at least one container valve 12. The container may consist of one or two glass bottles or plastic bag containers. Thus, a second container can quickly be selected as the first one is consumed by switching the container valve/valves 12. The pump system pressurizes the body cavity, which can be a knee, a shoulder, an elbow, a hip, a hand or a foot, via a feed line 13 and via an endoscope 14. There is a pressure drop over the feed line 13 and most particularly at the inlet and through the passage of the endoscope 14. The outflow device 3 can be an outflow liquid pump, an outflow shut off valve or a combination of an outflow shut off valve and an external suction source. In case the outflow device is a liquid pump, preferably of a peristaltic roller type, it removes the liquid via an instrument such as a shaver 15 or similarly type of instrument. The latter may be a cannula. The liquid is further withdrawn by the outflow device 3 through a tubing 16 into a waste container 17. Furthermore, the first control unit 4 is electrically connected to the outflow device 3 by an output device signal line 18.

The liquid coming out from the operating site through tubing 16 has been provided with a first optical sensor 21 arranged with a suitable wavelength adopted to identify blood cells, red blood cells, haemoglobin in the liquid coming out from the operating site through the tubing 16 and to give electrical signals to a second control unit 24, a clear vision module, indicating the actual amount of blood cells, red blood cells, haemoglobin in the liquid coming out from the operating site. The resulting automatic or manual action taken is an increase flow level at constant pressure for reducing the sight problem or an increase of the pressure level at constant flow level to stop bleeding or both.

The tubing 16 is also provided with a second optical sensor 22 to identify debris in the liquid coming out from the operating site through tubing 16 and to give electrical signals to the second control unit 24 indicating that there is debris in the liquid coming out from the operating site. Both the first optical sensor 21 and the second optical sensor 22 can be combined into the same housing. They are both sending its visibility signals to the clear vision module 24 in order to be correlated to a clear vision reference in the module and to regulate the flow values through the body cavity during the surgical procedures. Also a separate debris identification module 25, indicating debris in the liquid coming out from the operating site is provided for cooperation with one or both of the sensors 21, 22 and the second control unit 24, the clear vision module. Furthermore, a separate blood amount detector module 26 indicating the actual amount of blood cells, red blood cells, haemoglobin in the liquid coming out from the operating site is provided for cooperation with one or both of the sensors 21, 22 and the second control unit 24, the clear vision module. The interaction between the debris identification module 25, the blood amount detection module 26 and the second control unit 24 is indicated with double arrows. A third optical sensor 23 may be attached to the feed line 13 for calibration purposes of the first and second optical sensors as the saline solution in the feed line is crystal clear.

Note that the optical detectors 21, 22 may be fitted by the shaver 15 or similar instrument. This would further reduce the response time of the detection of blood and debris. Note also that the outflow device 3 is not necessary for the function of the clear vision purposes of FIG. 1. Furthermore, operating devices such as buttons, foot pedal and a remote device together with presentation devices is also provided but not indicated in the figure.

Figures 2, 2A, 2B, 2C:
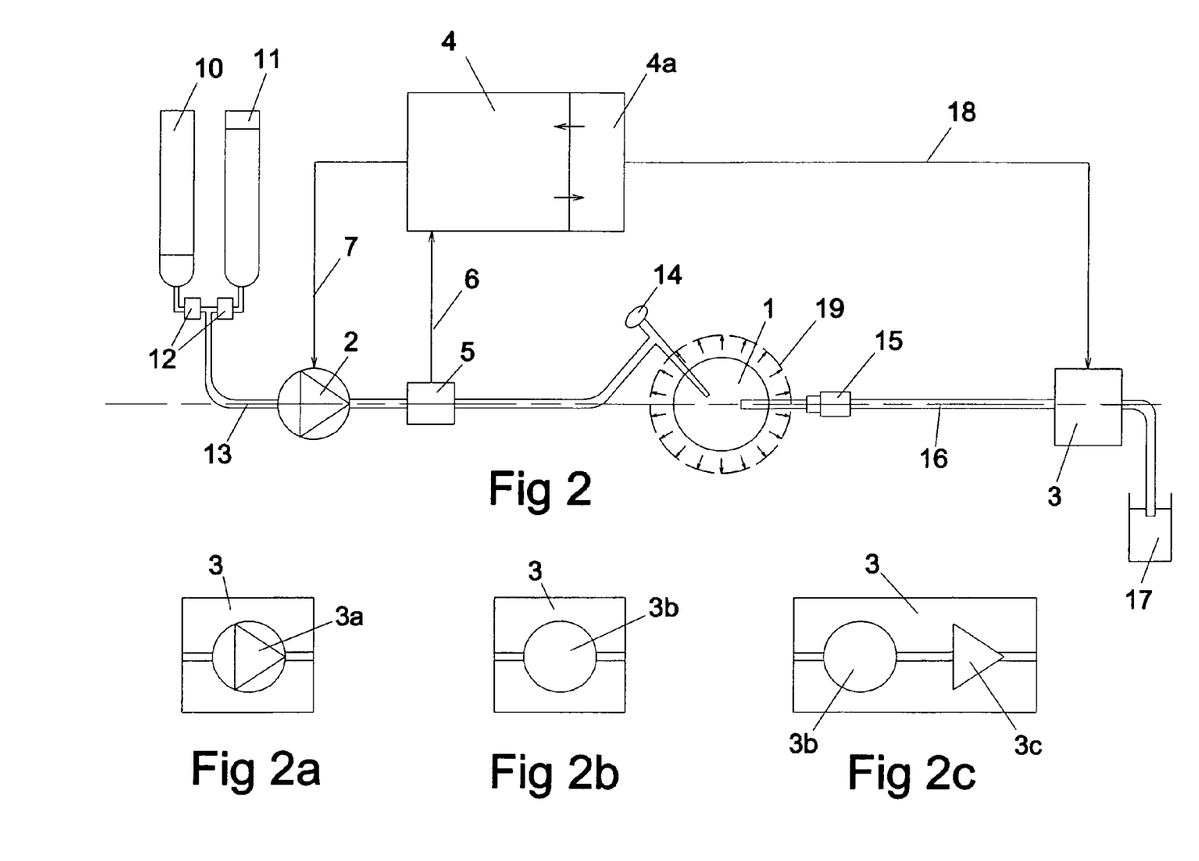
FIG. 2 shows a second feature of the invention.
FIG. 2a indicates a first embodiment of an outflow device.
FIG. 2b indicates a second embodiment of an outflow device.
FIG. 2c indicates a third embodiment of an outflow device.

FIG. 2 shows a basic configuration of a pump system for use in irrigating a body cavity 1 which pump system comprises an inflow liquid pump 2, an outflow device 3 and a first control unit 4 containing electronics with microcontroller for the drive of the pump heads, memory circuits including a calculating function unit 4a, front panel, power supply etc. The calculating function unit 4a serves as a reference for a feed back control system, indicated by the two arrows between the first control unit 4 and the calculating function unit 4a, in achieving real pressure values in the body cavity 1. The calculating function unit 4a compares the inflow irrigation liquid pressure and flow with pressures calculated to correspond to pressures in the body cavity 1 for the respective flow for a nominal surgical site. A pressure sensor 5 is electrically connected to the first control unit 4 by a signal line 6 through which an electric signal corresponding to the actual liquid pressure is delivered to the control unit. The first control unit 4 is also electrically connected to the inflow liquid pump 2 by an input pump signal line 7. The pump system withdraws saline from a first container 10 by means of the pump head of the inflow liquid pump 2, preferably being a peristaltic roller pump. The first container 10 may cooperate with a second container 11 by means of at least one container valve 12. The container may consist of one or two glass bottles or plastic bag containers. Thus, a second container can quickly be selected as the first one is consumed by switching the container valve/valves 12. The pump system pressurizes the body cavity, which can be a knee, a shoulder, an elbow, a hip, a hand or a foot, via a feed line 13 and via an endoscope 14. There is a pressure drop over the feed line 13 and most particularly at the inlet and through the passage of the endoscope 14. The outflow device 3, preferably of a peristaltic roller type, removes the liquid via an instrument such as a shaver 15 or similarly type of instrument. The latter may be a cannula. The liquid is further withdrawn by the outflow device 3 through a tubing 16 into a waste container 17. Furthermore, the first control unit 4 is electrically connected to the outflow device 3 by an output device signal line 18.

As is indicated in FIGS. 2a, 2b and 2c the outflow device is provided with three separate embodiments. In FIG. 2a the outflow device is an outflow liquid pump 3a. In FIG. 2b the outflow device is an outflow shut off valve 3b and in FIG. 2c the outflow device is a combination of an outflow shut off valve 3b and an external suction source 3c.

This basic configuration of a pump system makes it possible to maintain a pressure regulation in the body cavity in that the pressure sensor 5 indicates the actual pressure in the feed line 13, which actual pressure is compared to memorized pressure values in a static part of the calculating function unit 4a which actual pressure values correspond to empirical acquired real values in a table of a nominal body cavity, or calculated values. By the use of such calculating function unit 4a it is possible to obtain a constant actual pressure regulation in the body cavity in that the first control unit 4 also regulates the outflow liquid pump 3a. An increased flow value through the body cavity at constant pressure can be maintained by an increased speed of both the inflow liquid pump 2 and the outflow liquid pump 3a. An increased pressure value in the body cavity at constant flow can be maintained by an increased speed of the inflow liquid pump 2 holding the outflow liquid pump 3a at a constant speed. The surgical site of the body cavity will then expand as indicated by the arrows in FIG. 2 to an enlarged body cavity volume 19. This constant pressure control in the body cavity can be maintained automatically by the system when a change in liquid flow is initiated. Also a constant pressure control in the body cavity can be maintained automatically at an altered level by the system without a change of liquid flow through the body cavity.

A second part of this basic configuration of the pump system makes it possible to alter the function to compare the inflow irrigation liquid pressure and flow with pressures calculated to correspond to pressures in the body cavity for the respective flow for a nominal surgical site in order to work for a body cavity that does not follow the nominal default values. This is made as previously described in the following way by stopping both the inflow and outflow pumps 2, 3a instantaneous and then measuring the pressure difference during approximately two seconds in the trapped liquid volume between the inflow and outflow pumps 2,3a. It is to be noted that the invention is not limited to systems with an outflow pump. The outflow pump can alternatively be a shut off valve 3b. After this time period the measured pressure values can be mathematically extrapolated to the end pressure in the body cavity 1 and thus making up new values for an actual body cavity.

Figure 3:
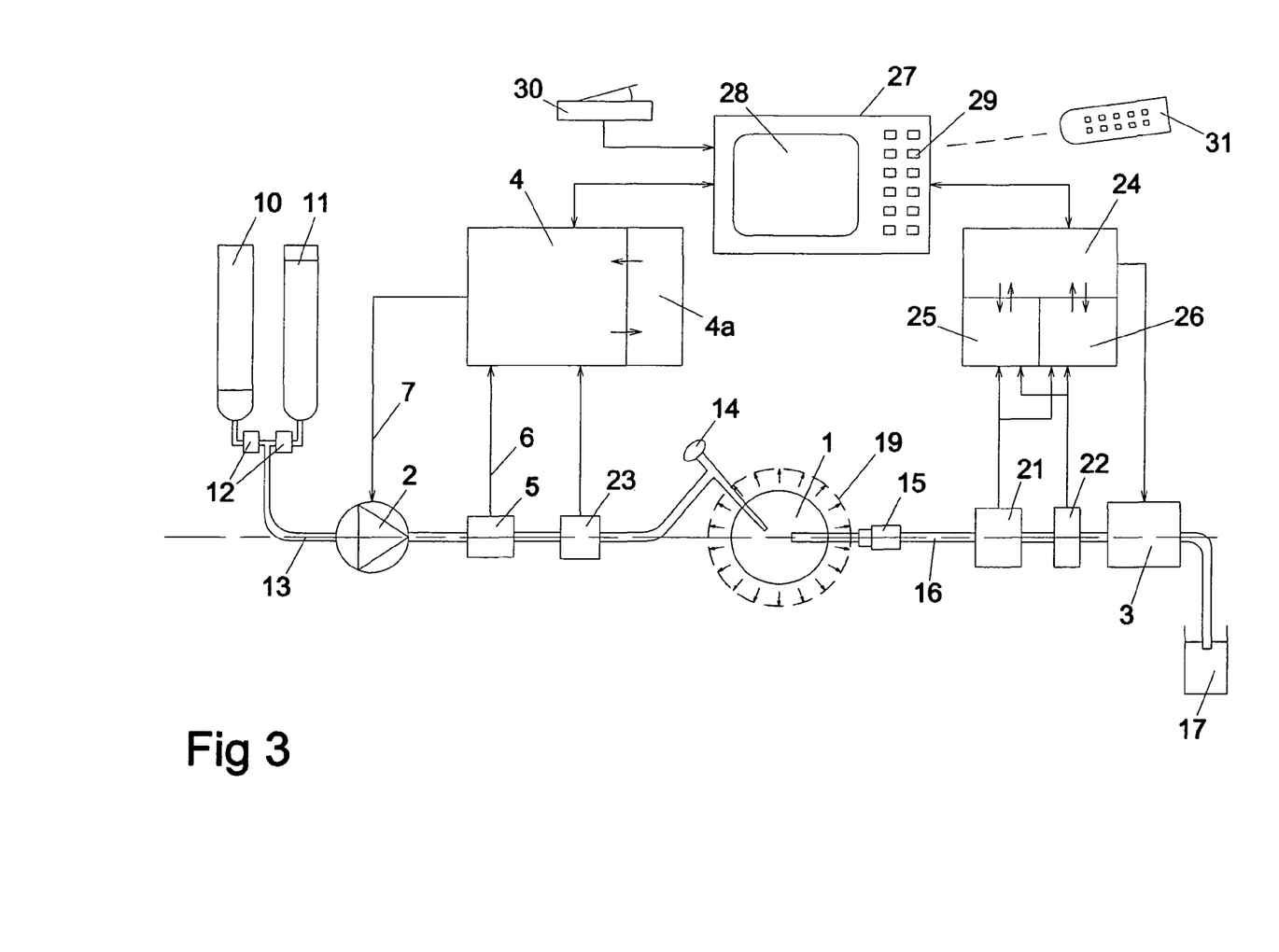
FIG. 3 shows a third feature of the invention.

FIG. 3 shows an alternative configuration of the invention where identical parts from FIGS. 1 and 2 have the same reference numbers. In addition to the basic configuration in FIG. 2 the area where liquid is coming out from the operating site through tubing 16 has been provided with a first optical sensor 21 arranged with a suitable wavelength adopted to identify blood cells, red blood cells, and haemoglobin in the liquid coming out from the operating site through the tubing 16 and to give electrical signals to a second control unit 24, a clear vision module, indicating the actual amount of blood cells, red blood cells, and haemoglobin in the liquid coming out from the operating site. The resulting automatic or manual action taken is an increased flow level at constant pressure for reducing the sight problem or an increase of the pressure level at constant flow level to stop bleeding or both.

The tubing 16 is also provided with a second optical sensor 22 arranged with another wavelength adopted to identify debris in the liquid coming out from the operating site through tubing 16 and to give electrical signals to the second control unit 24 indicating the actual amount of debris in the liquid coming out from the operating site. Both the first optical sensor 21 and the second optical sensor 22 can be combined into the same housing. They both send vision signals to the clear vision module 24 in order to be correlated to a pressure control in the module and to regulate the flow values through the body cavity during the surgical procedures as previously described. Also a separate debris identification module 25, indicating the amount of debris in the liquid coming out from the operating site, is provided for cooperation with one or both of the sensors 21, 22 and the second control unit 24, the clear vision module. Furthermore, a separate blood amount detector module 26 indicating the actual amount of blood cells, red blood cells, and haemoglobin in the liquid coming out from the operating site is provided for cooperation with one or both of the sensors 21, 22 and the second control unit 24, the clear vision module. The interaction between the debris identification module 25, the blood amount detection module 26 and the second control unit 24 is indicated with double arrows.

Note that the optical detectors 21, 22 may be fitted by the shaver 15 or similar instrument. This would further reduce the response time of the detection of blood and debris.

A third optical sensor 23 may be attached to the feed line 13 for calibration purposes of the first and second optical sensors as the saline in the feed line is crystal clear.

FIG. 3 also shows an operating control device 27 with a display 28 for presentation of the surgical area inside the body cavity and the various values for control over the surgical procedure. Operating devices such as buttons 29, foot pedal 30 and a remote device 31 are provided for the surgeon to alter flow, pressure, change levels of parameters, chose presetting of cavity type, service mode, alarms, etc. As can be seen in the figure the operating control device 27 operates both the first control unit 4 and the second control unit 24. Similar operating devices are also provided in the basic configuration of the pump system according to FIG. 1.

Figure 4:
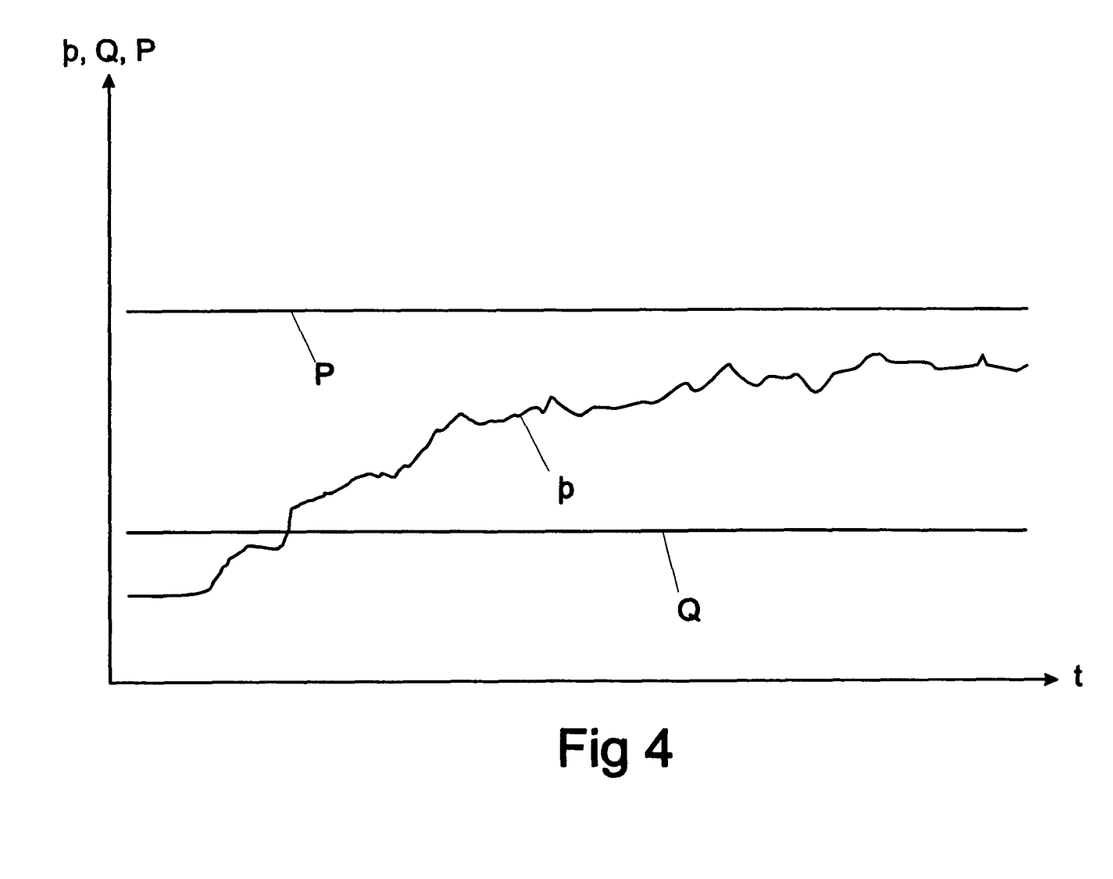
FIG. 4 shows an initial time diagram with optical sensing.

In FIG. 4, a time diagram describes the situation when blood or debris is emerging and increasing from the surgical site. The pump system comprises means to automatically increase flow through the surgical site, should blood or debris be detected. In this figure, the automated increase is not engaged. The curve P shows the pressure in the surgical site, and the flow curve Q represents the liquid flow through the surgical site. Both curves show constant values. The voltage signals from the optical sensors 21, 22 (in FIGS. 1 and 3) represents an optical density curve ♭ indicating increasing optical density from blood and/or debris. This would be the situation as more and more blood and/or debris is withdrawn from the surgical site. This is in all indicative of too much blood and/or debris in the surgical site, severely reducing visibility to the surgeon.

Figure 5:
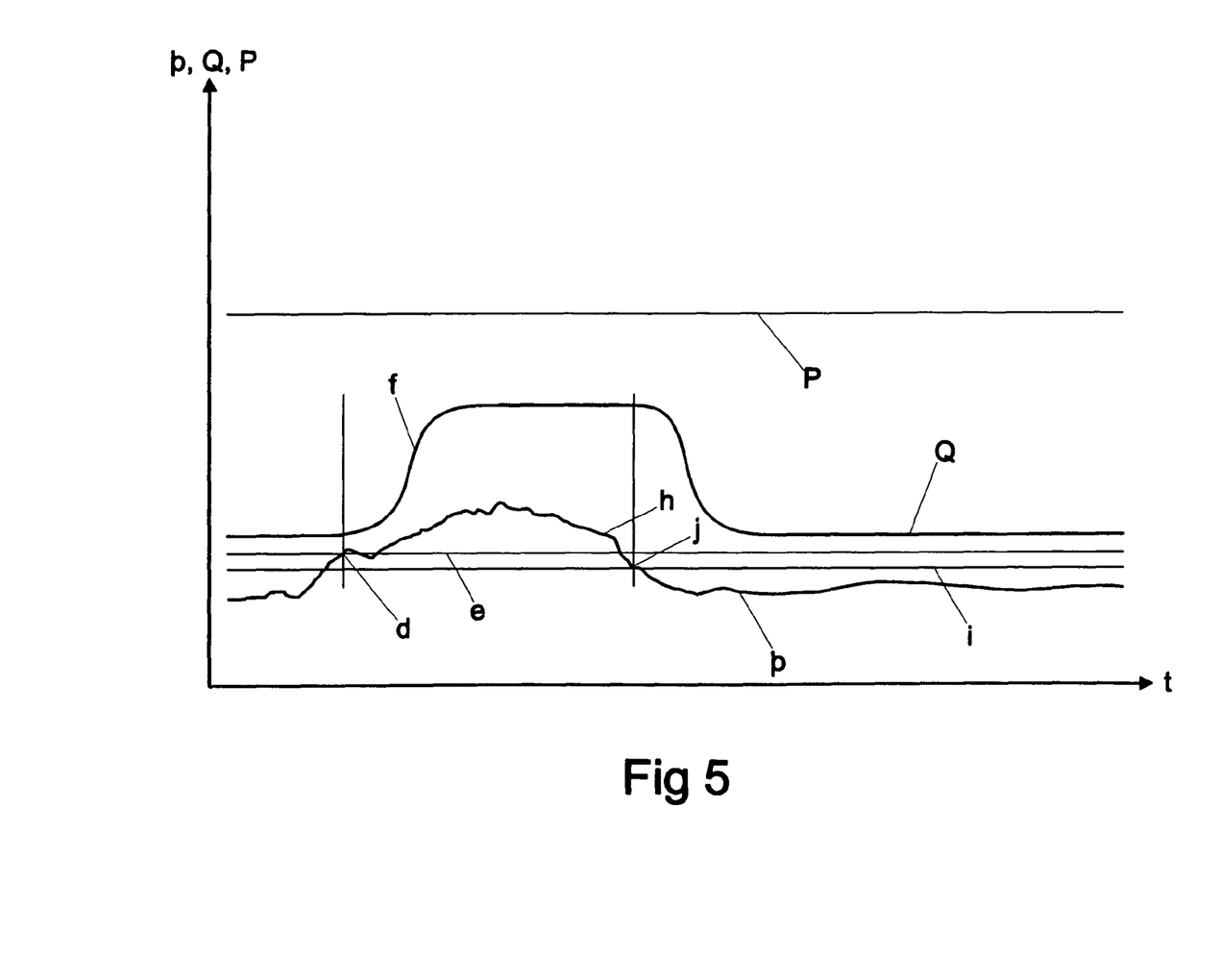
FIG. 5 shows a compensating debris time diagram according to FIG. 4.

In FIG. 5, a time diagram describes the situation when debris is emerging from the surgical site. The automated increase of flow when emerging debris is detected is now engaged. The pressure curve P shows a constant pressure which indicates that a constant pressure algorithm is active while the flow curve Q shows an increased flow. The voltage signals from the second optical sensor 22 (in FIGS. 1 and 3) representing an optical density curve ♭ indicates an increasing degree of blood and/or debris. At the time at d the voltage signal from the optical sensor is strong enough to indicate a disturbing amount of debris, and a first density trigger level e is reached. This trigger level is set at the manufacturing of the pump system, but may be adjusted by technical personnel if found necessary. This triggering appoints to the inflow and outflow pumps to elevate flow through the surgical site. This elevation of flow is shown at f on the flow curve Q. The pressure may optionally be elevated at this stage to eliminate bleeding at the surgical site. This elevation is part of the pressure regulating mechanism of the pump system, and is achieved by letting the inflow pump run faster than the outflow pump for the time necessary to elevate pressure. The elevated flow rinses the surgical site, so the optical density from debris will as a result fade as is shown at h. When the optical density has reached a second density trigger level i, at the time j, the increased flow can be normalized again, and the pressure—if elevated—may be also be normalized again, as the automated rinse process is finished.

Figure 6:
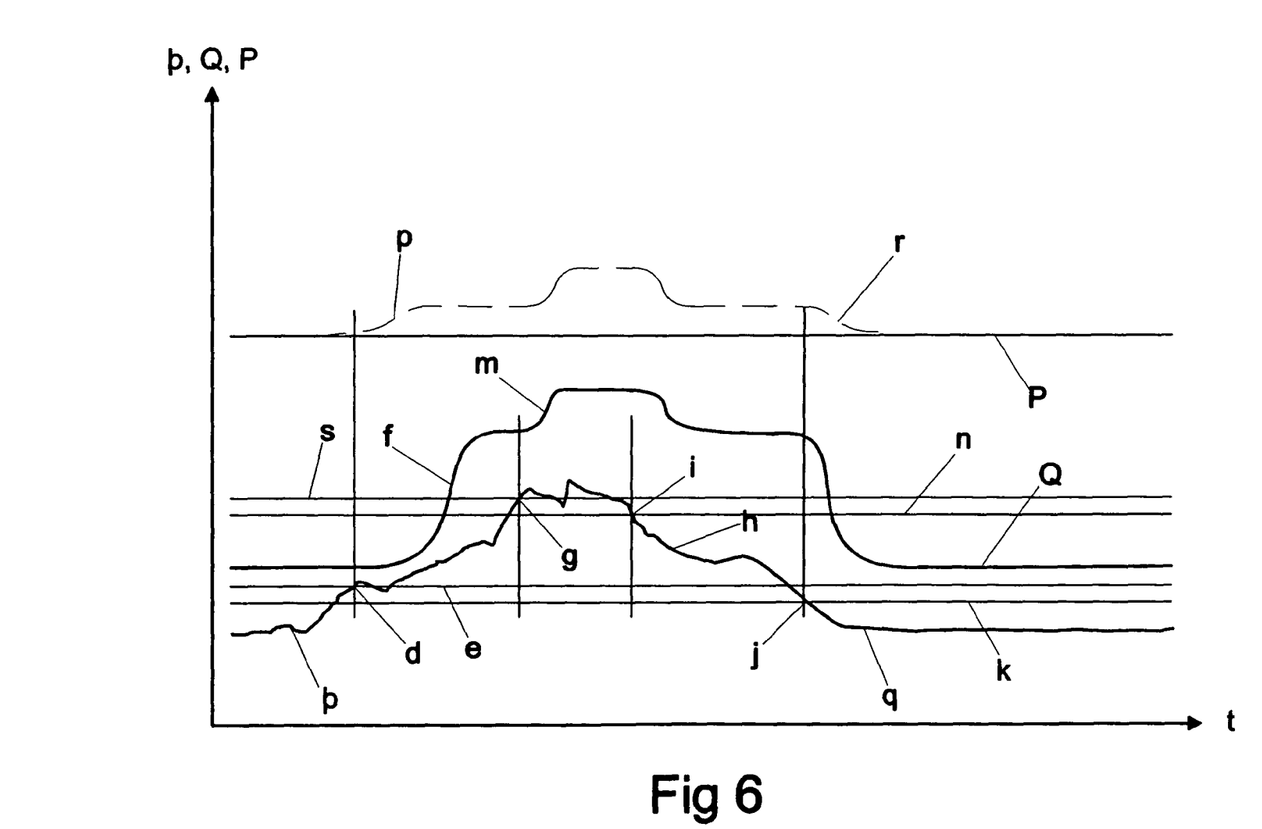
FIG. 6 shows a compensating red blood cells time diagram according to FIG. 4.

In FIG. 6, a time diagram over red blood cell detection describes the situation when a loss of blood from the surgical site is high. The automated increase of flow when emerging blood is detected is engaged. Again, the pressure curve is indicated by P, and the flow curve is indicated by Q. The voltage signals from the first optical sensor 21 (in FIGS. 1 and 3) represent an optical density curve ♭ indicating an increasing degree of blood. At the time d the voltage signal from the optical sensor is strong enough to indicate a disturbing amount of blood, as a first density trigger level e is reached. This appoints to the inflow and outflow pumps to elevate flow through the surgical site. This elevation of flow is shown at f on the flow curve Q. The pressure may optionally elevate at this stage indicated by p on the dotted part of the pressure curve P. As the degree of blood is severe, the optical density increases further so the signal voltage reaches a second density trigger level s at the time indicated by g. The flow is now elevated even higher as shown by the Flow curve Q at m. This results in sufficient rinsing of the surgical site. Now, the optical density will reduce and reach a third density trigger level n at the time i. The amount of blood is further reduced at the flange h on the optical density curve ♭. At the time j the optical density is reduced to a fourth density trigger level k which at last represents a normal situation with no or little blood. The increased flow can be normalized again, and the pressure—if elevated—may also be normalized again as indicated at r, as the automated rinse process is finished.

In detecting blood cells, red blood cells, and haemoglobin during a time interval and knowing the flow during this interval an indication of blood loss is established and registered by the blood amount detector module 26 which is valuable information to the surgeon.

Figure 7:
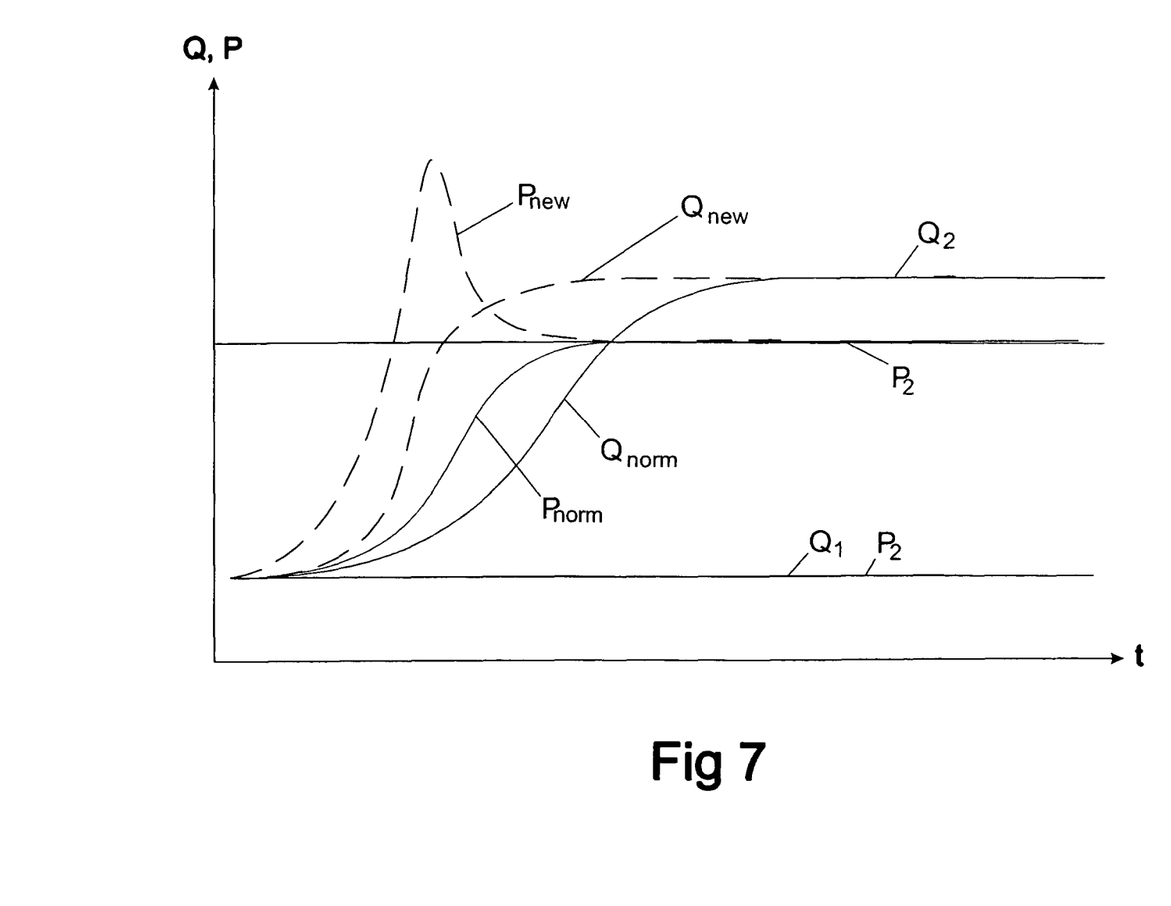
FIG. 7 shows an initiating flow and pressure diagram.

In FIG. 7 a situation is described when the flow Q is to be increased from a low flow value Q1 to a high flow value Q2 in the liquid path. The pressure P is increased from P1 to P2 as described in the timing diagram. The pressure curve $P_{new}$ describes a normal increase of pressure, resulting in a normal increase of flow as shown in the flow curve $Q_{norm}$. However, in the present invention, the pressure is rapidly elevated to a pressure far above the new pressure level $P_2$ and down to the pressure level of $P_2$ as described with pressure curve $P_{new'}$ resulting in a much quicker flow response indicated by the flow curve $Q_{new}$.

The invention claimed is:

1. A vision regulation device for a liquid for irrigation of a body cavity surgical site comprising,
    an inflow liquid pump arranged to feed an irrigation liquid from a container though a feed line into a body cavity,
    an outflow device, which is arranged to drain the irrigation liquid from the body cavity through a tubing,
    a first control unit connected to the inflow liquid pump,
    wherein the tubing is provided with optical sensors configured to be at an outflow site of the body cavity to identify an amount of blood cells, red blood cells, haemoglobin and debris in the irrigation liquid, and to give signals to a second control unit indicating the amount of blood cells, red blood cells, haemoglobin and debris,
    wherein the second control unit increases the effect of the inflow liquid pump and/or the outflow device to rinse the surgical site so that flow of the inflow irrigation liquid is increased when the amount of debris is increased in the irrigation liquid in, or coming out of, the surgical site or the inflow liquid pump is regulated so that pressure of the irrigation liquid is increased when the amount of blood cells, red blood cells or haemoglobin is increased in the irrigation liquid in, or coming out of, the surgical site.

2. The device according to claim 1, wherein a pressure sensor connected to the feed line is provided at an inflow site of the body cavity for measuring an inflow irrigation liquid pressure, and a matching device in the first control unit is configured to align the inflow irrigation liquid pressure with a pressure in the body cavity by altering the effect of the inflow liquid pump and/or the outflow device on pressure in the body cavity.

3. The device according to claim 2, wherein the outflow device is either an outflow liquid pump, or an outflow shut off valve or a combination of an outflow shut off valve and an external suction source.

4. The device according to claim 2, wherein a recalculation device is provided in the first control unit together with a calibration device for the pressure from the pressure sensor and flow values that compares the inflow irrigation liquid pressure and flow with pressures calculated to correspond to pressures in the body cavity for the respective flow and recalculates the pressure and flow at the surgical site by simultaneously stopping both the inflow liquid pump and the outflow device during a time interval and continuously registering the inflow irrigation liquid pressure of the pressure drop in the liquid volume between the inflow liquid pump and the outflow device during the time interval.

5. The device according to claim 2, wherein the first control unit is configured to compare the inflow irrigation liquid pressure and flow with pressures calculated to correspond to pressures in the body cavity for the respective flow for maintaining either a constant irrigation liquid pressure and/or a constant irrigation liquid flow in the body cavity at a value of inflow liquid pressure from the pressure sensor and flow that correspond to pressures in the body cavity for the respective flow by a control of both the inflow liquid pump and/or the outflow device for outflow liquid.

6. The device according to claim 1, further comprising a debris identification module for registering the amount of debris in the liquid coming out from the surgical site and a separate blood identification module for registering the amount of blood cells, red blood cells, and/or haemoglobin, wherein each of the identification modules is provided for cooperation with one or both of the sensors.

7. The device according to claim 1, wherein the optical sensors compare values of registered blood cells, red blood cells, haemoglobin and/or the amount of debris in the liquid coming out from the surgical site and compare these registered values with reference values in the second control unit.

* * * * *